(12) United States Patent
Leflein et al.

(10) Patent No.: US 6,417,206 B1
(45) Date of Patent: Jul. 9, 2002

(54) ANTITUSSIVE/ANTIHIST AMINIC/ DECONGESTANT COMPOSITIONS

(75) Inventors: Ronald Leflein, East Hanover; Alexander D. D'Addio, Piscataway, both of NJ (US)

(73) Assignee: MedPointe Healthcare Inc., New York, NY (US)

( * ) Notice: Subject to any disclaimer, the term of this patent is extended or adjusted under 35 U.S.C. 154(b) by 0 days.

(21) Appl. No.: 09/771,130

(22) Filed: Jan. 26, 2001

(51) Int. Cl.[7] .................. A61K 31/216; A61K 31/4402; A61K 31/137
(52) U.S. Cl. ................ 514/352; 514/530; 514/653
(58) Field of Search ............................ 514/352, 530, 514/653

(56) References Cited

U.S. PATENT DOCUMENTS 6,287,597 B1  9/2001  Gordziel .................. 424/464
6,306,904 B1  10/2001 Gordziel .................. 514/530

FOREIGN PATENT DOCUMENTS

JP          64007786    *  8/1993

OTHER PUBLICATIONS

Luchem, DrugLaunch (Accession No.: 94: 41007) Jul. 29, 1991.*

Weiler et al., Ann. Allergy, 64(1), 63–67 1990 (abstract).*

* cited by examiner

Primary Examiner—Phyllis G. Spivack
(74) Attorney, Agent, or Firm—Elliot M. Olstein; Raymond E. Stauffer

(57) ABSTRACT

Tannate compositions are disclosed consisting essentially of carbetapentane tannate, pyrilamine tannate and phenylephrine tannate are effective when administered orally for the symptomatic relief of cough associated with respiratory tract conditions such as the common cold, bronchial asthma, acute and chronic bronchitis.

14 Claims, No Drawings

ANTITUSSIVE/ANTIHISTAMINIC/DECONGESTANT COMPOSITIONS

FIELD OF INVENTION

The invention relates to novel antitussive/antihistiminic/decongestant tannate compositions. The compositions contain as essential ingredients carbetapentane tannate, pyrilamine tannate and phenylephrine tannate.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid, the internal ester of gallic acid also frequently referred to as tannin.

Tannic Acid consists of an amorphous powder glistening scales or spongy masses varying in color from yellowish-white to light brown. Tannic acid is very soluble in water, glycerine or alcohol.

Tannic acids are usually obtained from glycosides which consist of several molecules of a tannic acid in combination with glucose.

Commercially available, tannic acid, also known as Tannin, has a complex non-uniform chemistry, usually contains from about 5% to about 10% by weight water, has a molecular weight of about 1700, and is typically produced from Turkish or Chinese nutgall.

Carbetapentane, known chemically as 2-[2-(diethylamino)ethoxy]ethyl 1-phenylcyclopentanecarboxylate is an antitussive compound that is described in U.S. Pat. No. 2,842,585 and is structurally related to caramiphen. Carbetapentane citrate has a melting point of 93° C. and occurs as a white powder freely soluble in water and slightly soluble in alcohol.

Carbetapentane has an atropine-like action that depresses the cough reflex by selective central nervous system depression.

Pyrilamine is one of the oldest and most enduring antihistaminic drugs, known chemically as N-[(4-methoxyphenyl)methyl]-N',N'-dimethyl-N-2-pyridinyl-1,2-ethanediamine, its preparation is disclosed in U.S. Pat. No. 2,502,151 and is an oily liquid. Pyrilamine hydrochloride salt is very soluble in water and has a melting point of 143–143.5° C. whereas the maleate salt is slightly soluble in water, benzene and ether and has a melting point of 100–101° C.

Phenylephrine, known chemically as (-)-m-hydroxy-α-[(methylamino)-methyl] benzyl alcohol, is a synthetic, optically active sympathomimetic amine which has one hydroxyl group on the benzene ring. The hydroxyl group is placed in the position meta to the aliphatic side chain. The meta position affords optimal activity and phenylephrine (neo-synephrine) replaced an older preparation, synephrine, in which the hydroxyl was in the para position.

Phenylephrine hydrochloride is available in the form of the levorotatory isomer, a white, odorless, non-hygroscopic, crystalline compound possessing a bitter taste. Phenylephrine hydrochloride has a melting point of 140–145° C. and is freely soluble in water and alcohol.

Antitussive, antihistamine and decongestant compounds in the form of their free bases as well as their salts, e.g. hydrochloride, citrate, maleate, tannate, etc., are well known. Antitussives, antihistamines and decongestants in the form of their tannate salts are very desirable because such salts are generally stable and may be combined in such form without any untoward side effects.

Antitussives, antihistamines and decongestants in the form of their tannate salts are typically prepared by reacting the free base, e.g. carbetapentane, pyrilamine, phenylephrine, etc. with tannic acid in the presence of a volatile solvent, usually isopropanol. Typically, in the conventional isopropanol route, the antitussive, antihistaminic or decongestant free base and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. No. 5,599,846 and U.S. Pat. No. 5,663,415.

THE INVENTION

It has now been found that the novel combination of carbetapentane tannate, pyrilamine tannate and phenylephrine tannate produces a composition having antitussive, antihistaminic and sympathomimetic decongestant properties superior to the use of any one of the tannate compounds alone.

The compositions of the present invention may be prepared for oral administration in the form of powders, capsules, elixirs, syrups and the preferred forms of tablets or suspensions formulated so that ideally each tablet contains approximately 50 to 75 mg of carbetapentane tannate, preferably about 60 mg of carbetapentane tannate, approximately 30 to 50 mg pyrilamine tannate, preferably about 40 mg of pyrilamine tannate, and approximately 5 to 15 mg phenylephrine tannate, preferably about 10 mg phenylephrine tannate or that ideally each 5 mL (approximately 1 teaspoon) of suspension would contain approximately 20 to 30 mg carbetapentane tannate, preferably 30 mg of carbetapentane tannate, 25 to 30 mg pyrilamine tannate, preferably 30 mg of pyrilamine tannate, and 3 to 8 mg of phenylephrine tannate, preferably 5 mg of phenylephrine tannate.

Tablets containing the unique tannate combination of the present invention are prepared in a conventional manner by the addition of suitable pharmaceutical carriers including fillers, diluents, colorants, lubricants and the like as well as conventional and well known binding and disintegrating agents. A typical tablet composition of the present invention containing starch, dibasic calcium phosphate, colorants, magnesium stearate, methylcellulose, polygalacturoic acid, povidone and talc as described in Example 1 which follows is prepared by well known conventional tabletting techniques such as those disclosed in U.S. Pat. Nos. 3,018,221; 2,798,024 and 2,757,124.

EXAMPLE 1

Carbetapentane Tannate, Pyrilamine Tannate and Phenylephrine Tannate Tablets

| Ingredient | Milligrams per Tablet |
| --- | --- |
| Carbetapentane Tannate | 60.0 |
| Pyrilamine Tannate | 40.0 |
| Phenylephrine Tannate | 10.0[1] |

-continued

| Ingredient | Milligrams per Tablet |
| --- | --- |
| Starch, NF | 65.0 |
| Methylcellulose, USP | 150 |
| Polygalacturoic Acid | 32.0 |
| Dibasic Calcium Phosphate, USP, Dihydrate | 65.0 |
| Povidone, USP | 25.0 |
| Talc, USP | 5.4 |
| FD&C Red #40 Aluminum Lake-40% | 3.93 |
| Magnesium Stearate, NF | 4.0 |
| Alcohol Specially Denatured 23A 190 Proof | 140[2] |

[1]5% excess added during manufacturing
[2]Not present in the finished tablet product Suspensions of the compositions of the present invention are prepared in a conventional manner such that each 5 mL (one teaspoon) contains:

| | |
| --- | --- |
| Carbetapentane Tannate | 30 mg |
| Pyrilamine Tannate | 30 mg |
| Phenylephrine Tannate | 5 mg |

The suspension formulations additionally contain benzoic acid, colorants, natural and artificial flavors, glycerin, kaolin, magnesium aluminum silicate, methylparaben, pectin, purified water, saccharin, sodium hydroxide and sucrose or sorbitol.

Example 2, which follows, is illustrative of a typical suspension formulation of the present invention prepared by conventional well known compounding techniques.

EXAMPLE 2

Carbetapentane Tannate, Pyrilamine Tannate and Phenylephrine Tannate Suspension

| Ingredient | Milligrams per 5 mL |
| --- | --- |
| Carbetapentane Tannate | 30.0 |
| Pyrilamine Tannate | 30.0[1] |
| Phenylephrine Tannate | 5.0[2] |
| Pectin, USP (Medium Viscosity) | 50.0 |
| Kaolin, USP (Colloidal Powder) | 1000 |
| Magnesium Aluminum Silicate, NF | 35.0 |
| Benzoic Acid, USP | 10.0 |
| Methylparaben, NF | 2.5 |
| Sucrose, NF | 1000 |
| Saccharin Sodium, USP | 0.75 |
| Glycerin, USP | 225 |
| Flavor Black Currant Imitation | 0.91 |
| Flavor Strawberry with Other Natural Flavors | 2.28 |
| Purple Shade "R" Dye | 0.45 |
| FD&C Red #3 Dye | 0.8 |
| FD&C Yellow #5 | 0.3 |
| Sodium Hydroxide Solution-50% | 0.793[3] |
| Purified Water, USP (Deionized) adjust to | 5 mL |

[1]5% excess added during manufacturing
[2]15% excess added during manufacturing
[3]The quantity of Sodium Hydroxide Solution may be varied depending on the pH of the Kaolin used in the batch. Tannic acid may also be used in lieu of sodium hydroxide solution for pH adjustment. Sodium Citrate, USP, Dihydrate and Citric Acid, USP, Anhydrous may also be included in the formula for pH adjustment.

For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed:

1. A therapeutic composition for the symptomatic relief of cough associated with adverse respiratory tract conditions in warm-blooded animals in need of such treatment said composition comprising pharmaceutically effective amounts of active ingredients, wherein said active ingredients consist of carbetapentane tannate, pyrilamine tannate and phenylephrine tannate.

2. The therapeutic composition of claim 1 in tablet form.

3. The therapeutic composition of claim 2 wherein each tablet contains 50 to 75 mg of carbetapentane tannate, 30 to 50 mg of pyrilamine tannate and 5 to 15 mg of phenylephrine tannate.

4. The therapeutic composition of claim 2 wherein said tablet form contains about 60 mg of cabetapentane tannate, about 40 mg of pyrilamine tannate, and about 10 mg of phenylephrine tannate.

5. The therapeutic composition of claim 1 in suspension form.

6. The therapeutic composition of claim 5 wherein 5 ml. of the suspension contain 20 to 30 mg of carbetapentane tannate, 25 to 30 mg of pyrilamine tannate and 3 to 8 mg of phenylephrine tannate.

7. The therapeutic composition of claim 5 wherein said suspension form contains about 30 mg of cabetapentane tannate, about 30 mg of pyrilamine tannate, and about 5 mg of phenylephrine tannate, per 5 ml.

8. A method for symptomatically treating and relieving the distress of cough associated with adverse respiratory tract conditions in warm-blooded animals comprising orally administering to warm-blooded animals in need of such treatment the composition of claim 1.

9. The method of claim 8 wherein said composition is in tablet form.

10. The method of claim 9 wherein each tablet contains 50 to 75 mg of carbetapentane tannate, 30 to 50 mg of pyrilamine tannate and 5 to 15 mg of phenylephrine tannate.

11. The method of claim 9 wherein said tablet form contains about 60 mg of cabetapentane tannate, about 40 mg of pyrilamine tannate, and about 10 mg of phenylephrine tannate.

12. The method of claim 8 wherein said composition is a suspension.

13. The method of claim 12 wherein 5 ml. of the suspension contain 20 to 30 mg of carbetapentane tannate, 25 to 30 mg of pyrilamine tannate and 3 to 8 mg of phenylephrine tannate.

14. The method of claim 12 wherein said suspension contains about 30 mg of cabetapentane tannate, about 30 mg of pyrilamine tannate, and about 5 mg of phenylephrine tannate, per 5 ml.

* * * * *